(12) United States Patent
Bordignon et al.

(10) Patent No.: US 9,068,016 B2
(45) Date of Patent: Jun. 30, 2015

(54) CONJUGATES FOR THE TREATMENT OF MESOTHELIOMA

(71) Applicants: Claudio Bordignon, Milan (IT); Antonio Lambiase, Milan (IT)

(72) Inventors: Claudio Bordignon, Milan (IT); Antonio Lambiase, Milan (IT)

(73) Assignee: Molmed S.P.A, Milan (IT)

( * ) Notice: Subject to any disclaimer, the term of this patent is extended or adjusted under 35 U.S.C. 154(b) by 0 days.

(21) Appl. No.: 13/750,682

(22) Filed: Jan. 25, 2013

(65) Prior Publication Data

US 2013/0315856 A1    Nov. 28, 2013

Related U.S. Application Data

(62) Division of application No. 12/992,524, filed as application No. PCT/EP2009/055704 on May 12, 2009, now abandoned.

(30) Foreign Application Priority Data

May 13, 2008    (EP) .................................... 08008872

(51) Int. Cl.

| | | |
|---|---|---|
| A61K 38/19 | (2006.01) | |
| A61K 38/08 | (2006.01) | |
| A61K 38/10 | (2006.01) | |
| A61K 38/12 | (2006.01) | |
| C07K 14/25 | (2006.01) | |
| C07K 7/64 | (2006.01) | |
| C07K 7/06 | (2006.01) | |
| C07K 7/08 | (2006.01) | |
| C07K 14/525 | (2006.01) | |
| A61K 38/20 | (2006.01) | |
| A61K 38/21 | (2006.01) | |
| A61K 47/48 | (2006.01) | |

(52) U.S. Cl.
CPC ............. *C07K 14/525* (2013.01); *A61K 38/191* (2013.01); *A61K 38/208* (2013.01); *A61K 38/217* (2013.01); *A61K 47/48246* (2013.01); *C07K 7/06* (2013.01)

(58) Field of Classification Search
None
See application file for complete search history.

(56) References Cited

U.S. PATENT DOCUMENTS

| | | | |
|---|---|---|---|
| 4,950,646 A * | 8/1990 | Wallner et al. ............... | 514/16.7 |
| 6,406,858 B1 * | 6/2002 | Petry et al. ..................... | 435/7.1 |
| 7,109,303 B2 * | 9/2006 | Corti ........................... | 530/387.3 |
| 2003/0207247 A1 * | 11/2003 | Stassinopoulos et al. ........ | 435/2 |

OTHER PUBLICATIONS

Takagi et al. A long-term survivor case of malignant mesothelioma treated by recombinant tumor necrosis factor-SAM2 (TNF-alpha mutein) and 5-fluorouracil (5-FU): a new therapeutic approach based on host-tumor relationship. Anticancer Res. Nov.-Dec. 1998;18(6B):4591-600.*
Handbook of Pharmaceutical Excipients, 2nd Edn., Eds. Wade & Weller, 1994, American Pharmaceutical Association.
Janne P. A. et al., "Sorafenib in malignant mesothelioma (MM): A phase II trial of the Cancer and Leukemia Group B (CALGB 30307)" 2007, J Clin. Oncol. (Meeting Abstracts), 25:7707.
Oken M. M. et al., "Toxicity and response criteria of the Eastern Cooperative Oncology Group," 1982, Am. J. Clin. Oncol., 5:649-655.
Bowman et al., "Chemosensitivity and cytokine sensitivity of malignant mesothelioma," 1991, Cancer Chemother Pharmacol., 28:420-426.
Ohnuma et al., "Effects of natural interferon α, natural tumor necrosis factor α and their combination on human mesothelioma xenografts in nude mice," 1993, Cancer Immunol Immunother., 36:31-36.

* cited by examiner

*Primary Examiner* — David Romeo
(74) *Attorney, Agent, or Firm* — McDonnell Boehnen Hulbert & Berghoff LLP

(57) ABSTRACT

The present invention provides conjugates of cytokines and targeting peptides that is able to bind to a receptor expressed on tumor-associated vessels or to a component of the extracellular matrix associated to the tumor vessels, for treatment of malignant pleural mesothelioma. In particular, the invention provides conjugates comprising the cytokine TNF linked to a peptide containing the NGR motif. The invention further provides pharmaceutical compositions comprising such conjugate and pharmaceutical formulations comprising conjugates dissolved in appropriate buffers.

11 Claims, No Drawings

CONJUGATES FOR THE TREATMENT OF MESOTHELIOMA

This application is a divisional of U.S. application Ser. No. 12/992,524 filed on Feb. 7, 2011 which is a national stage application of International Application No. PCT/EP2009/055704, filed on May 12, 2009, which claims priority to European application Serial No. EP 08008872.7, filed on May 13, 2008, all of which are herein incorporated by reference in their entireties.

FIELD OF THE INVENTION

The present invention relates to cancer therapy, particularly, to the use of conjugates of cytokines and targeting peptides for the treatment of Malignant Pleural Mesothelioma (MPM). More particularly, the invention relates to the use of a conjugate comprising a peptide containing NGR motif and TNF (NGR-TNF) for the treatment of MPM.

BACKGROUND

Malignant pleural mesothelioma (MPM) is a rare aggressive neoplasm that arise primarily from the surface serosal cells of the pleural cavities, generally associated to a poor prognosis. The incidence of MPM is increasing throughout the world, and it is expected to rise in the next 10-20 years because of the increasing exposure to asbestos in past years.

There is no standard of care for the treatment of MPM, and only a minority of patients are eligible for any potentially curative therapy. Complications of cytotoxic chemotherapy strongly influence physician decisions in the treatment of older (65 years of age and older) and/or poor performance status (PS≥2) patients because of the occurrence of frequent and serious co-morbidity events that can complicate therapy (Repetto, J. Support Oncol. 2003, 1(4 Suppl. 2):18-24). Performance status (PS) according to Eastern Cooperative Oncology Group (ECOG, Robert Comis M.D., Group Chair), are scales and criteria used by doctors and researchers to assess how a patient's disease is progressing, to assess how the disease affects the daily living abilities of the patients and determine appropriate treatment and prognosis (Oken, et al. 1982 Am J Clin Oncol 5:649-655). Performance status 2 identifies "ambulatory patients capable of all selfcare but unable to carry out any work activities. Up and about more than 50% of waking hours". Demographic aspects as described above, have to taken into account in the treatment of mesothelioma patients considering that the median age of disease onset is 74 years and that more than 50% of patients have a performance status of 2 or worst at diagnosis (Chapman et al. Thorax 2008, 63(5):435-439).

Over the past 20 years, several approaches have been studied, even if platinum containing regimen demonstrated a greater activity than nonplatinum containing combination, their effects seems to be modest in term of progression free survival (a relatively strong predictive parameter of survival), survival and toxicities (Fennell et al. Nat. Clin. Pract. Oncol. 2008, 5(3): 136-147).

Current progress and clinical data on MPM treatment are reviewed in Ceresoli et al. The Oncologist 2007, 12:850-863. Single modality therapies (surgery, radiotherapy and chemotherapy) have failed to prolong patient survival.

Pemetrexed disodium in combination with cisplatin is the first and only chemotherapy agent that has been granted a marketing approval for the treatment of chemotherapy naïve patients with unresectable malignant pleural mesothelioma. However, this chemotherapeutic approach achieved only a modest increase in terms of progression-free (5.7 versus 3.9 months) and overall survival (12.1 versus 9.3 months) in comparison with cisplatin monochemotherapy. Moreover, this chemotherapy combination even if performed in selected patient population (median age 60 years old, Karnofsky performance status at least of 70, that identifies a patient that cares for self and is unable to carry on normal activity or to do active work; or even greater performance status) was unexpectedly toxic and resulted in several treatment related deaths. Toxicity was due to interference with homocysteine metabolism and lead to a change in the protocol, by adding the prophylactic use of vitamin B12 and folate, as a supplementation to therapy. The incidence of serious toxicities with pemetrexed plus cisplatin fully-vitamins supplemented, in the Intent to Treat (ITT) population, was higher compared with the population treated with cisplatin alone (Vogelzang et al. J Clin Oncol 2003, 21 (14): 2636-2644).

At the present time, several biological agents have been evaluated in phase II clinical trials but none resulted to be effective, even if tested in front line and in combination therapy, showing in some circumstances, an unsafe toxicity pattern. Clinical investigations have been focused on epidermal growth factor receptor (EGFR) that is highly expressed in MPM (Destro et al. Lung Cancer 2006; 51:207-215; Edwards et al Lung cancer, 2006; 54:399-407) and on vascular endothelial growth factor (VEGF) and platelet-derived growth factor (PDGF) that are important autocrine growth factors in this disease. The use of inhibitors of these receptors has been investigated for the first-line treatment of mesothelioma.

Particularly, in a phase II clinical trial the EGFR inhibitor gefitinib (Iress®), approved for the treatment of advanced non small cell lung cancer, and showing a marked anti-proliferative effect on mesothelioma cells in vitro (Janne et al., Cancer Res 2002, 62:5242-5247), resulted not active as front-line therapy, with a median progression free survival less than three months, although 97% of patients with mesothelioma had EGFR overexpression (Govindan et al. Clin Cancer Res, 2005; 11:2300-2304). In this study gefitinib showed a class specific toxicity profile with the most common grade 3 adverse events (grade 3: severe side-effects) being represented by diarrhoea, skin rash and fatigue.

Likewise, Imatinib (Glivec®), a 2-phenylaminopyrimidine tyrosine kinase inhibitor known to affect both c-Kit and PDGF alpha and beta receptors and approved for the treatment of chronic myeloid leukaemia, didn't show to be effective as front-line single-agent therapy in terms of time to tumour progression (<3 months). Moreover, treatment was interrupted in the 40% of patients due to side effects. The main side effects were oedema (ankles, face, genitals and lungs) sometimes causing exacerbation of pleural or abdominal effusions, nausea and vomiting (Mathy et al. Lung cancer 2005 50:83-86).

The use of angiogenesis inhibitors has been investigated (Ceresoli et al. The Oncologist 2007, 12:850-863). A certain activity was reported with SU5416, a highly selective receptor tyrosine kinase inhibitor that targets the VEGF receptors Flt-1 and KDR/Flk, hampered by an excessive risk for thrombosis.

Valatanib (PTK787) a VEGF and PDGF receptor tyrosine kinases inhibitor showed a median progression free survival of 4 months, when administered to chemotherapy-naïve patients as front-line therapy. Grade 3/4 toxicities (grade 3: severe side-effects, grade 4: life threatening or disabling side-effects) resulted in gastrointestinal bleeding, neutropenia, lymphopenia, nausea/vomiting, increased ALT/AST, hypertension (Jahan et al., J. Clin. Oncol., 2006 ASCO Annual Meeting Proceedings Part I. Vol. 24, No 18S (June supplement), 2006: 7081).

Bevacizumab, a recombinant human anti-VEGF monoclonal antibody that blocks the binding of VEGF to its receptors, was evaluated as front-line treatment combined with chemotherapy in a double-blind, placebo controlled, randomized phase II trial. The combination of bevacizumab plus cisplatin and gemcitabine (BGC) in previously untreated patients did not reach the primary study end point, without any significant improvement in median progression-free survival (6.9 months for BGC vs 6.0 months for chemotherapy alone, p=0.88) or median overall survival (15.6 months for GCB vs 14.7 mo for chemotherapy alone, p=0.91). Moreover a statistically significant higher incidence of different toxicities consisting of alopecia, hypertension, epistaxis, proteinuria, stomatitis, and non neutropenic infection was observed in the bevacizumab arm (Karrison et al., J Clin Oncol. 25 (18S (June 20 Supplement)), 2007: 7526).

All the clinical trials performed so far show that even drugs such as imatinib or gefitinib, already approved for the treatment of certain types of tumors, are not active in mesothelioma. Moreover, drugs resulting to be effective in mesothelioma preclinical models have no activity in humans. These data confirm that the antitumor activity of a drug against certain types of tumor is not predictive of its antitumor activity in another cancer type. Different types of cancer affecting different organs have different aetiology, different underlying spectrum of molecular alterations and a different way of growing. A skilled person is not able to predict whether or not a drug resulting to be effective for the treatment of a tumor would be active against another tumor type.

Currently, there are no standard treatments available for patients progressing following first-line chemotherapy in MPM. This patient population has a very aggressive disease with a median progression-free survival of 1.5 months reported with the use of best supportive care only (Jassem et al., J Clin Oncol. 2008; 26(10):1698-704). The recurrent tumor is almost invariably more resistant to a second-line of treatment than it was at first presentation and treatment (Broxterman et al., Drug Resist Updat. 2003; 6(3):111-27). Moreover patients tolerability to a further line of treatment is generally worse than after first-line chemotherapy (Berthold et al., J Clin Oncol. 005; 23(32):8247-8252).

The aim of a second-line treatment is not only the effectiveness in cancer treatment but also a relative safe and low toxicity profile for the patients.

Several agents have been studied in second-line treatment of mesothelioma, but no improvement of efficacy and toxicity has been observed.

Recently, a randomized, multicentre phase III trial examining pemetrexed plus best supportive care versus best supportive care alone in previously treated mesothelioma patients has been reported. Although a statistically significant longer time to disease progression was demonstrated in the chemotherapy-receiving arm (3.7 months, 95% 2Cl:3.0-4.4) versus the best supportive care arm (1.5 months, 95% Cl:1.4-1.7), no improvement in overall survival was shown (8.4 versus 9.7 months, respectively). The most frequent grade 3/4 toxicities were primarily hematologic and non -hematologic toxicities such as febrile neutropenia and fatigue (Jassem et al., J Clin Oncol 2008; 26(10):1698-704).

In a single-arm, multi-centre Phase II study the combination of bevacizumab plus erlotinib was explored in patients with unresectable mesothelioma who had previously received one prior chemotherapy regimen. Unfortunately, there were no clinical responses in this clinical trial, with a time to tumor progression of 2.7 months. The toxicity profile was characterized by several grade 3 toxicities including skin rash, diarrhoea, thrombosis (Jackman et al., J Thorac Oncol 2007; 2 (8):5602). In another single-arm, multi-centre Phase II study, patients who were either treatment naive or had previously received chemotherapy were treated with the multi-targeted tyrosine kinase inhibitor sorafenib. Among pre-treated patients, the median failure-free survival was 3.6 months. Grade 3/4 toxicity resulted in hand foot reaction and fatigue (Janne P. et al., J Clin Oncol 2007; 25 (18S): Abstract 7707).

Therefore, there is a need of effective drugs, having a favorable toxicity profile, for the treatment of mesothelioma. The present invention addresses this need. We surprisingly found that conjugates comprising a targeting peptide and a cytokine are effective for the treatment of Malignant Pleural Mesothelioma and that such conjugates have a well tolerated toxicity profile.

WO 01/61017 discloses a conjugation product between TNF or IFNγ and a ligand of the CD13 receptor, particularly a peptide containing the NGR motif. Data disclosed in the patent show that TNF conjugates are effective in the treatment of lymphoma and melanoma mouse models. In addition, conjugates of IFNγ and a peptide containing the NGR motif have a potent antitumor effect in lymphoma and fibrosarcoma mouse models (Curnis et al., Cancer Res. 2005; 65(7):2906-2913). Conjugates of various cytokines and tumor targeting moieties have been disclosed (WO 03/092737), and it has been demonstrated (WO 03/093478) that pharmaceutical compositions comprising such conjugates are effective at extremely low dosage that does not induce activation of negative feedback mechanism. WO 2006/067633 discloses peptides containing degradation products of the NGR motif, that are able to target the αvβ3 integrin, and conjugates comprising these peptides and cytokines. None of these document discloses the effectiveness of cytokine conjugates for the treatment of Malignant Pleural Mesothelioma.

SUMMARY OF THE INVENTION

The present invention is related to the field of cancer therapy and particularly to the treatment of Malignant Pleural Mesothelioma.

Currently the reference regimen as front line therapy is the combination of cisplatin plus pemetrexed, an aggressive chemotherapeutic approach with a modest increase in term of progression free survival and median survival and serious toxic effects. More importantly, given the natural history of disease, with most patients dying within one year of diagnosis, the availability of new agents in the second-line setting assumes major importance. Unfortunately, there are no standard treatments available for patients progressing following first-line chemotherapy in MPM, and best supportive care remains the reference approach for these patients.

Several new drugs have been investigated both as single agent or in combination, but none of them resulted to be effective. Particularly no increase of progression free and overall survival has been reported to date, whereas high incidences of grade 3 (severe side-effects) or 4 (life threatening or disabling side-effects) toxicity have been observed in phase II and phase III clinical trials.

We have surprisingly found that the administration of a conjugate comprising a targeting peptide and a cytokine is effective for the treatment of mesothelioma, particularly in terms of increase of progression free survival and well tolerated toxicity profile of the conjugate.

Particularly it has been observed that the administration of a conjugate comprising the targeting peptide CNGRC linked through the amino acid G (glycine) to human TNF brings about a clinical benefit in patients refractory or resistant to standard first-line chemotherapy regimen. Preliminary analysis on patients enrolled in the first-stage of trial has shown that 7 patients (44%; 95% confidence interval (CI) 20-68%) had a stable disease (SD) as best response, with a median duration of 4.4 months (range, 1.6-7.1+ months) The estimated progression-free survival rate at 4.5 months was 37% (95% CI 10-65%) and 3 patients (19%) were progression free at 6 months.

After the end of the study, the overall results obtained by treating 57 patients has shown that NGR-hTNF doubled the progression free survival observed with best supportive care that is the reference treatment for this patient population lacking a standard therapy. In addition, the results obtained with NGR-hTNF in terms of progression free survival are comparable with those obtained with combination therapies, such as gemcitabine plus vinorelbine or bevacizumab plus erlotinib with the advantage of administering only one drug that does not have the toxicities associated with those drugs.

Such data show that conjugates of cytokines and targeting peptides can be successfully used for the treatment of mesothelioma, even as second line treatment of patients refractory or resistant to chemotherapy regimen, that means effective even in a more resistant tumor than it was at first presentation and treatment.

Furthermore, low dose administration (0.8 µg/m$^2$) in both triweekly or weekly schedule, was associated with a manageable and favorable toxicity profile, with only one patient (2%) experiencing a grade 3 toxicity and neither grade 4 adverse events nor treatment-related death reported so far. Main grade 1 (mild side-effects) or 2 (moderate side-effects) toxicities per patient were transient infusion-related constitutional symptoms, including chills (lasting approximately 15-30 minutes). The observed low toxicity profile is a key advantage in the treatment of mesothelioma, particularly considering that the median age of disease onset is 74 years.

Therefore the aim of a second line treatment i.e. effectiveness in terms of progression free survival and low toxicity profile for patients, is completely achieved through the use of the conjugates of the present invention for the treatment of mesothelioma, and clearly indicates their effective use in a first line treatment.

STATEMENTS OF THE INVENTION

According to one aspect of the invention there is provided a conjugate comprising a targeting peptide and a cytokine for use in the treatment of mesothelioma.

Preferably the cytokine is TNFα, TNFβ, IFNγ, IL12.

According to a preferential aspect of the invention there is provided a conjugate wherein the targeting peptide is a peptide containing the NGR or isoDGR or RGD motives.

Preferably the targeting peptide is a peptide containing the NGR motif.

More preferably the targeting peptide is selected from the group consisting of linear or cyclic CNGRCVSGCAGRC (SEQ ID No. 1), NGRAHA (SEQ ID No. 2), GNGRG (SEQ ID No. 3), CVLNGRMEC (SEQ ID No. 4), CNGRC (SEQ ID No. 5), CNGRCG (SEQ ID No. 6), LNGRE (SEQ ID No. 7), YNGRT (SEQ ID No. 8), LQCICTGNGRGEWKCE (SEQ ID No. 9), LQCISTGNGRGEWKCE (SEQ ID No. 10), CICTGNGRGEWKC (SEQ ID No. 11), CISTGNGRGEWKC (SEQ ID No. 12), MRCTCVGNGRGEWTCY (SEQ ID No. 13), MRCTSVGNGRGEWTCY (SEQ ID No. 14), CTCVGNGRGEWTC (SEQ ID No. 15) and CTSVGNGRGEWTC (SEQ ID No. 16).

According to a preferred aspect of the invention there is provided a conjugate wherein the cytokine is TNF linked to the targeting peptide CNGRC through a spacer. Preferably the spacer is G (glycine).

According to a further aspect of the invention there is provided a method for treating mesothelioma comprising administering a conjugate comprising a targeting peptide and a cytokine for the treatment of mesothelioma.

According to another aspect of the invention there is provided a pharmaceutical composition comprising an effective amount of a conjugate comprising a targeting peptide and a cytokine, together with pharmaceutically acceptable carriers and diluents.

According to a preferred aspect of the invention there is provided a pharmaceutical composition comprising an effective amount of a conjugate comprising TNF linked to the targeting peptide CNGRC through the spacer G, together with pharmaceutically acceptable carriers and diluents.

More preferably the pharmaceutical compound is for the treatment of mesothelioma.

According to a further aspect of the invention there is provided a pharmaceutical formulation containing a conjugate comprising TNF linked to the targeting peptide CNGRC through the spacer G at concentration in the range of 0.01 to 10 mg/ml together with pharmaceutically acceptable carriers and diluents.

Preferably the pharmaceutical formulation consists of 0.150 mg/ml of a conjugate comprising TNF linked to the targeting peptide CNGRC through the spacer G dissolved in a solution of 50 mM $Na_2HPO_4$, 150 mM NaCl.

DETAILED DESCRIPTION OF THE INVENTION

A detailed description of preferred features and embodiments of the invention will be described by way of non-limiting example.

The invention can be put into practice by a person of ordinary skill in the art that will employ, unless otherwise indicated, conventional techniques of chemistry, molecular biology, microbiology, recombinant DNA and immunology. All such techniques are disclosed and explained in published literature. See, for example, J. Sambrook, E. F. Fritsch, and T. Maniatis, 1989, Molecular Cloning: A Laboratory Manual, Second Edition, Books 1-3, Cold Spring Harbor Laboratory Press; Ausubel, F. M. et al. (1995 and periodic supplements; Current Protocols in Molecular Biology, ch. 9, 13, and 16, John Wiley & Sons, New York, N.Y.); B. Roe, J. Crabtree, and A. Kahn, 1996, DNA Isolation and Sequencing: Essential Techniques, John Wiley & Sons; J. M. Polak and James O'D. McGee, 1990, In Situ Hybridization: Principles and Practice; Oxford University Press; M. J. Gait (Editor), 1984, Oligonucleotide Synthesis: A Practical Approach, Irl Press; and, D. M. J. Lilley and J. E. Dahlberg, 1992, Methods of Enzymology: DNA Structure Part A: Synthesis and Physical Analysis of DNA Methods in Enzymology, Academic Press. All these publications are incorporated by reference.

Targeting Peptides

The term "peptide" as used herein includes polypeptides and proteins. The term complexes where individual constituent polypeptides are linked by covalent or non-covalent means. The term "polypeptide" includes peptides of two or more amino acids in length, typically having more than 5, 10, 20, 30, 40, 50 or 100, amino acids.

Peptides that can be employed in the invention may include aminoacids in D or L configuration. Moreover, modified peptides can be used, for example to reduce immunogenicity, to increase circulatory half-life in the body of the patient, to enhance bioavailability and/or to enhance efficacy and/or specificity.

A number of approaches have been disclosed to modify peptides for therapeutic application. Peptides can be linked to a variety of polymers, such as polyethylene glycol (PEG) and polypropylene glycol (PPG) (see for example U.S. Pat. Nos. 5,091,176, 5,214,131 and U.S. Pat. No. 5,264,209) or to bifunctional crosslinkers, such as N-succinimidyl 3-(2pyridyldithio) propionate, succinimidyl 6-[3-(2 pyridyldithio) propionamido]hexanoate, and sulfosuccinimidyl 6-[3-(2 pyridyldithio)propionamido]hexanoate (see U.S. Pat. No. 5,580,853).

As used herein, the term targeting peptide means a peptide as previously defined, that is able to bind to a receptor expressed on tumor-associated vessels or to a component of the extracellular matrix associated to the tumor vessels.

The targeting peptide of the conjugate may be targeted to the following receptors: CD13/Aminopeptidase N or integrins.

Aminopeptidases are a large group of enzymes involved in a number of biological processes such as maturation, regulation and degradation of proteins and polypeptides. In particular, in vitro and in vivo studies have recently demonstrated that aminopeptidase N (CD13/APN), the receptor for amino acid sequence NGR plays multiple roles in angiogenesis and is critical for the development of new blood vessels from existing vessels in pathological conditions, whereas it is not essential for de novo blood vessel formation in embrio-fetal development and normal adult function (Pasqualini, Koivunen et al. 2000; Arap, Kolonin et al. 2002 Bhagwat, Landenranta et al. 2001; Bhagwat, Petrovic et al. 2003; Fukasawa, Fujii et al. 2006; Rangel, Sun et al. 2007).

Therefore in a preferred embodiment the targeting peptide is a peptide containing the NGR motif. Peptide containing the NGR motif and the method for identifying such peptides are disclosed in WO 98/10795 and WO 99/13329 that are here incorporated by reference.

In a particularly preferred embodiment, the targeting peptide is selected from the group consisting of linear or cyclic CNGRCVSGCAGRC (SEQ ID No. 1), NGRAHA (SEQ ID No. 2), GNGRG (SEQ ID No. 3), CVLNGRMEC (SEQ ID No. 4), CNGRC (SEQ ID No. 5), CNGRCG (SEQ ID No. 6), LNGRE (SEQ ID No. 7), YNGRT (SEQ ID No. 8), LQCICTGNGRGEWKCE (SEQ ID No. 9), LQCISTGNGRGEWKCE (SEQ ID No. 10), CICTGNGRGEWKC (SEQ ID No. 11), CISTGNGRGEWKC (SEQ ID No. 12), MRCTCVGNGRGEWTCY (SEQ ID No. 13), MRCTSVGNGRGEWTCY (SEQ ID No. 14), CTCVGNGRGEWTC (SEQ ID No. 15) and CTSVGNGRGEWTC (SEQ ID No. 16).

An integrin molecule is composed of two noncovalently associated transmembrane glycoprotein subunits called α and β. Because the same integrin molecule in different cell types can have different ligand-binding specificities, it seems that additional cell-type specific factors can interact with integrin modulate their binding activity. α and β subunits can combine in different ways to form integrin receptors. Natural ligands of integrin are adhesive proteins of the extracellular matrix proteins such as fibronectin, vitronectin, collagens, laminin.

Many integrins, particularly αvβ3 integrin, recognize the amino acid sequence RGD (arginine-glycine-aspartic acid). In a further embodiment the targeting peptide is a peptide able to bind to the αvβ3 integrin, particularly a peptide containing the RDG motif.

Other ligands of avi33 integrin are peptides containing degradation products of the NGR motif. Details of these peptides are disclosed in WO 2006/067633 incorporated herein by reference. In a further embodiment the targeting peptide are peptides containing the degradation product of the NGR motif, particularly peptides containing the isoDGR motif.

In a particularly preferred embodiment, the targeting peptides are selected from the group consisting of linear or cyclic CisoDGRCVSGCAGRC (SEQ ID No. 17), isoDGRAHA (SEQ ID No. 18), GisoDGRG (SEQ ID No. 19), CVLisoDGRMEC (SEQ ID No. 20), CisoDGRC (SEQ ID No. 21), CisoDGRCG (SEQ ID No. 22), LisoDGRE (SEQ ID No. 23), YisoDGRT (SEQ ID No. 24), LQCICTGisoDGRGEWKCE (SEQ ID No. 25), LQCISTGisoDGRGEWKCE (SEQ ID No. 26), CICTGisoDGRGEWKC (SEQ ID No. 27), CISTGisoDGRGEWKC (SEQ ID No. 28), MRCTCVGisoDGRGEWTCY (SEQ ID No. 29), MRCTSVGisoDGRGEWTCY (SEQ ID No. 30), CTCVGisoDGRGEWTC (SEQ ID No. 31) or CTSVGisoDGRGEWTC (SEQ ID No. 32).

Conjugates

The present invention relates a to the use of a conjugate comprising a targeting peptide linked to a cytokine for the treatment of mesothelioma. A non-limiting list of cytokines that can be used in the conjugate of the present invention is TNFα, TNFβ, IFNα, IFNβ, IFNγ, IL-I, 2, 4, 6, 7, 12, 15, EMAP II, vascular endothelial growth factor (VEGF), PDGF, PD-ECGF or a chemokine.

Preferably the cytokine is TNFα, TNFβ, IFNγ, IL12.

As used herein, the term the term "linked" means that the targeting peptide is associated the cytokine through a chemical coupling so as to form a fusion protein wherein the first sequence (the targeting peptide) is able to transport the second sequence to a target cell. Therefore, the targeting peptide of the conjugate is linked to the cytokine via their polypeptide backbone and the resulting fusion protein is obtained through genetic expression in host cells of a DNA sequence encoding these protein, or direct synthesis of proteins or coupling of pre-formed sequences associated by a cross-linking agent.

The targeting peptide can be directly linked to the cytokine or indirectly through a spacer. The spacer can be a single amino acid or amino acid sequence or an organic residue for example 6-aminocapryl-N-hydroxysuccinimide.

In one embodiment, the targeting peptide preferably is linked to the cytokine N-terminus or C-terminus in order to avoid any interference in the binding of the cytokine to its receptor. Alternatively, the peptide can be linked to amino acid residues which are amido- or carboxylic-bonds acceptors, naturally occurring on the molecule or artificially inserted with genetic engineering techniques. The conjugate is prepared by use of a cDNA comprising a 5'-contiguous or a 3' contiguous sequence encoding the peptide.

TNF-α

TNF-α: Human INF-α is a 233 aa residue, nonglycosylated polypeptide that exists as either a transmembrane or soluble protein. When expressed as a 26 kDa membrane bound protein, TNF-α consists of a 29 aa residue cytoplasmic domain, a 28 aa residue transmembrane segment, and a 176 aa residue extracellular region. The soluble protein is created by a proteolytic cleavage event via an 85 kDa TNF-alpha converting enzyme (TACE), which cleaves a fragment of 76 aa (residues 1-76 of the 233 aa sequence) and generates a 17 kDa, 157 aa residue molecule that normally circulates as a homotrimer. The sequence of TNF-α transmembrane and soluble protein can be found at ExPASy (Expert Protein Analysis System) proteomics server of the Swiss Institute of Bioinformatics, www.expasv.com, UniProtKB/Swiss-Prot database, entry P01375.

TNF-α is a pleiotropic transmembrane protein, with a broad spectrum of cellular and tissutal biologic activities, which range from enhancement of proliferation to direct cytotoxicity on tumour cells, activation of innate and adaptative immune response and effects on endothelium (Watanabe, Niitsu et al. 1988; Fajardo, Kwan et al. 1992).

According to a preferred aspect of the invention, there is provided a conjugation product between TNF and the CNGRC peptide in which, preferably, the amino-terminal of TNF is linked to the peptide, preferably through a spacer for use in the treatment of mesothelioma. Preferably the spacer is G (glycine).

IFNγ

Interferon-γ(IFN-γ), is a pleiotropic cytokine mainly produced by T-lymphocytes and natural killer cells (Farrar, et al., 1993; Boehm et al., 1997) promote anti-tumor responses. IFNγ exists as a homodimer of two noncovalently bound polypeptide subunits. The sequence of human IFN-γ can be found at NCBI (www.ncbi.nlm.nih.gov) website, Protein database, accession AAB59534.

IFN-γ is able to promote antitumor response by inducing antiproliferative and pro-apoptotic effects on many tumor cell types, by inhibiting tumor angiogenesis and activating natural killer cells and macrophages against tumor cells.

According to a preferred aspect of the invention, there is provided the use of a conjugation product between IFNγ and the CNGRC peptide, in which, preferably, the amino-terminal of IFNγ is linked the peptide, preferably through a spacer, preferably the spacer is G (glycine) for the treatment of mesothelioma.

IL12

IL12 (p70) is a glycosylated heterodimer composed of disulfide-linked p40 and p35 subunits, encoded by two separate genes. The correct heterodimer assembly occurs inside the producing cells. 1L12 induces IFNγ and other downstream proteins including the IFNγ-inducible protein 10 (IP10) and the monokine induced by IFNγ (Mig), activates immune responses and inhibits angiogenesis. Antitumor activity has been observed following IL12 peritumoral administration or by using tumor cells genetically modified to produce IL12. The sequence of human IL12 can be obtained from the NCBI (www.ncbi.nlm.nih.gov) website, Protein database, accession numbers M65271 (human p35 subunit) and M65272 human (p40 subunit).

Pharmaceutical Formulation

It is further object of the present invention a pharmaceutical formulation for treating an individual wherein the formulation comprises a therapeutically effective amount of a conjugate comprising a targeting peptide and a cytokine. In a preferred aspect the pharmaceutical formulation comprises a conjugate of the cytokine TNF linked to the targeting peptide CNGRC through the spacer G (glycine), in a particularly preferred aspect the formulation is for the treatment of mesothelioma.

Optionally the formulation may comprise a pharmaceutically acceptable carrier, diluent, excipient or adjuvant. The choice of pharmaceutical carrier, excipient or diluent can be selected on the basis of intended route of administration and standard pharmaceutical practice. The pharmaceutical formulation may comprise as—or in addition to—the carrier, excipient or diluent any suitable binder(s), lubricant(s), suspending agent(s), coating agent(s), solubilising agent(s), and other carrier agents that may aid or increase the viral entry into the target site (such as for example a lipid delivery system). Suitable carriers and diluents include isotonic saline solutions, for example phosphate-buffered saline. A description of the excipients that can be used in the invention may be found in The Handbook of Pharmaceutical Excipients, 2nd Edn, Eds Wade & Weller, American Pharmaceutical Association. The formulation of the invention may be for parenteral, intramuscular intravenous, subcutaneous, intraocular, oral or transdermal administration. In a preferred aspect of the invention, the formulation is for parenteral administration, in the form of a sterile aqueous solution which may contain other substances, for example enough salts or monosaccharides to make the solution isotonic with blood. Formulations for parenteral administration comprise injectable solutions or suspensions and liquids for infusions. For the preparation of the parenteral forms, an effective amount of the active ingredient will be dissolved or suspended in a sterile carrier, optionally adding excipients such as solubilizers, isotonicity agents, preservatives, stabilizers, emulsifiers or dispersing agents, and it will be subsequently distributed in sealed vials or ampoules.

Pharmaceutical formulations will be prepared for the administration daily, weekly or monthly in order to obtain the desired dosage. The formulations can be prepared for a administration every 2, 4, 6, 8, 10 or 12 hours.

The routes of administration and dosage regimens described are intended only as a guide since a skilled practitioner will be able to determine the actual dosage which will be most suitable for an individual subject on the basis of age, weight and response of the particular individual.

Treatment

The conjugates, compositions and formulations of the present invention will be used in the therapeutic treatment of mesothelioma. As used herein the word treatment include curative, palliative and prophylactic treatment.

EXAMPLE 1

Preparation of NGR-hTNF

Human recombinant NGR-TNF consisting of human soluble TNFα1-157 linked to the C-terminus of the targeting peptide CNGRCG, was prepared by recombinant DNA technology and purified as described in WO01/61017 incorporated herein by reference.

Formulation of NGR-TNF

Purified human recombinant NGR-TNF has been formulated to obtain a medicinal product to be administered in patients. Pharmaceutical formulation consists in recombinant human NGR-TNF at concentration in the range of 0.01 to 10 mg/ml dissolved in phosphate buffered saline in 3 ml type I glass vials 1 ml/vial.

The preferred formulation of the concentrate for solution for infusion is showed in Table 1.

TABLE 1

| formulation of NGR-hTNF | | | |
|---|---|---|---|
| Ingredient | | Concentration | Function |
| NGR-hTNF | | approx. 0.15 mg/nnl | Active ingredient |
| PBS | Na$_2$HPO$_4$ | 50 mM | Diluent |
| | NaCl | 150 mM | |
| | WFI | // | |

The medicinal product is stored at −80° C.

Before infusion to patients, NGR-hTNF in phosphate buffered saline (PBS) is diluted to the appropriate concentration with 0.9% NaCl containing 1 mg/ml human serum albumin (HSA). The presence of HSA is necessary to avoid loss of NGR-hTNF, when present at very low concentrations, by absorption to vessels and tubing.

EXAMPLE II

NGR-hTNF for the Treatment of Mesothelioma

Patient Selection

Informed, consenting patient (pts) were included in the study if they had histological or cytological confirmation of epithelial, sarcomatoid, and mixed malignant plural mesothelioma (MPM), with lesions measurable by computed tomography (CT) scan or magnetic resonance imaging (MRI) according to the modified RECIST criteria for malignant mesothelioma.

TABLE 2 performance status according to
Eastern Cooperative Oncology Group (ECOG)

| Grade | ECOG |
|---|---|
| 0 | Fully active, able to carry on all pre-disease performance without restriction |
| 1 | Restricted in physically strenuous activity but ambulatory and able to carry out work of a light or sedentary nature, e.g., light house work, office work |
| 2 | Ambulatory and capable of all selfcare but unable to carry out any work activities. Up and about more than 50% of waking hours |
| 3 | Capable of only limited selfcare, confined to bed or chair more than 50% of waking hours |
| 4 | Completely disabled. Cannot carry on any selfcare. Totally confined to bed or chair |
| 5 | Dead |

Patients were required to be at the least 18 years old of age, previously treated with no more than one systemic therapeutic regimen (prior intrapleural cytotoxic agent therapy including bleomycin is not considered systemic), they had no prior chemotherapy or radiotherapy within 28 days or surgery within 14 days before of study entry; ECOG performance status 0-2 (see table 2 for definitions of performance status); adequate baseline bone marrow, hepatic and renal function, defined as: neutrophils >1.5×10$^9$/L and platelets >100×10$^9$/L, bilirubin <1.5× upper limit of normal (ULN), aspartate aminotransferase (AST) and/or alanine aminotransferase (ALT) <2.5×ULN in absence of liver metastasis, AST and/or (ALT) <5×ULN in presence of liver metastasis, serum creatinine <1.5×ULN; absence of any conditions in which hypervoleamia and its consequences (e.g. increased stroke volume, elevated blood pressure) or haemodilution could represent a risk for the patient; normal cardiac function and absence of uncontrolled hypertension.

Patients were excluded if they had concurrent anticancer therapy; received any other investigational agent while on the study; clinical sign of central nervous system involvement; active or uncontrolled systemic disease/infection, serious illness or medical conditions which were incompatible with the protocol; know hypersensitivity/allergic reaction to human albumin preparation or to any of the excipients; any psychological, familial, sociological or geographical condition potentially hampering compliance with the study protocol. Pregnant or lactating woman were not included in the study (women of childbearing potential had to provide a negative pregnancy test within 14 days prior registration) or are those patients no practicing effective contraceptive measures thought the study.

Study Design and Statistical Methods

The study was planned as multicenter phase II single arm, open-label, non-randomized study conducted using Simon's two-stage design method with 16 and 27 patients to be enrolled in the first and second stage, respectively.

The primary endpoint of this study was antitumor activity defined as progression free survival (PFS). Secondary end point included tumor growth control rate (TGCR), overall survival (OS) and safety. Experimental imaging (DCE-MRI) and pharmacokinetics studies were also included.

Toxicity was registered according the NCI Common Toxicity Criteria version 3.0 grading system.

Considering the favourable toxicity profile, the protocol was subsequently amended to explore a more dense schedule of administration of NGR-hTNF given at same dosage of 0.8 μg/m$^2$ on a weekly basis. According to protocol amendment, in the case that ≤ 1 of first 6 patients experienced any grade 4 hematologic or grade 3-4 nonhematological toxicity during the first three weeks with the exclusion of nausea, vomiting, and fever that can be rapidly controlled with appropriate measures, 6 additional patients would have been enrolled to test the feasibility of this weekly schedule on a larger cohort. Globally, this schedule was considered safe if 2 of 12 patients experience any grade 4 hematologic or grade 3-4 non-hematologic toxicity. Moreover if after the end of treatment there were patients who discontinued treatment prematurely due to toxicity, follow-up would continue until completion of the study until any further related toxicity has resolved or upon clinical judgment. If applicable, in case of patients who discontinued treatment for any other reason than toxicity and before documented disease progression, follow up was planned every 8 weeks for clinical evaluation and disease evaluation until the first sign of progression or start of a new anticancer treatment.

Treatment Plan

Patients received NGR-hTNF at dose of 0.8 μg/m$^2$ by a 60-minute iv infusion every 3 weeks (q3w) or weekly. In presence of chills, according to the judgment of the investigator, treatment with paracetamol was allowed as prophylaxis for the subsequent cycles. No formal dose modification was required. The duration of the treatment was related to the clinical outcome (documented by RECIST criteria). In case of stable disease or objective response the treatment was continued until progressive disease, unacceptable toxicity, patient refusal, or physician decision.

Patient Assessment

The patient baseline assessment included initial medical evaluation as well chemistry and instrumental examinations. All investigations had to be performed within 14 days before the start of treatment and consisted on a complete evaluation of the medical history, physical examination including vital signs such as blood pressure, body temperature and evaluation of all clinical symptoms as well as ECOG performance status, electrocardiograms (ECG); complete blood counts was performed to include red blood cells, hemoglobin, hematocrit, total white blood cells, neutrophils, lymphocytes, monocytes, eosinophils, basophils and other, platelets. Serum chemistry assessment was performed, including prothrombin time (PT, INR), partial thromboplastin time (PTT), creatinine, urea, total bilirubin, albumin, glucose, alkaline phosphatase (ALP), uric acid, lactate dehydrogenases (LDH), γ-glutamyl-transpeptidase (γGT), ALT, AST, electrolytes (Na$^+$, K$^+$, Ca$^{++}$).

Tumor assessment was ensured according to modified RECIST criteria for malignant mesothelioma. HIV, HBV, HCV screening tests were performed only at baseline if applicable by the local guideline. A serum pregnancy test was required in women of reproductive potential.

During the treatment, patients were evaluated with a physical examination as well as ECOG performance status, ECG (if clinically relevant), complete blood counts and serum chemistry including the same parameters as described for baseline performed before each cycle.

Tumor assessment was evaluated every 6 weeks: all sites that were found to be involved at the initial assessment were re-investigated by the same method, all lesions chosen as target during the initial assessment were measured by the same method and, if possible, by the same person.

Results

First Stage Analysis

The first-stage analysis was performed on the first 16 patients enrolled and treated, on a total of 42 patients recruited into the study during the first year. Patients received NGRhTNF at dose of 0.8 µg/m$^2$ by a 60-minute iv infusion every 3 weeks (q3w). Approximately 75% of patients were males; the median age was 64 years old (range 48 to 80 years); ECOG performance status is 0 (7 pts) 1 (6 pts) and 2 (3 pts) respectively. Most of the patients (69%) had epithelial MPM in comparison with sarcomatoid (12.5%), mixed (6%) and unknown (12.5%) histologically confirmed MPM. Overall, 58 cycles (median 2, range 1-9) were completed. Seven patients (44%; 95% CI 20-68%) had a stable disease (SD) with a median duration of 4.4 months (range 1.6-7.1+). The maximum changes of target lesion in SD patients ranged from 17% shrinkage to 6% growth. The estimated PFS rate at 4.5 months was 37% (95% CI 10-65%) and three patients (19%) were progression free at 6 months.

Main grade 1-2 toxicities per patient were infusion-related constitutional symptoms including chills (56%) and fatigue (31%). Neither grade 3-4 treatment—related adverse event nor toxicity—related death were observed.

Second Stage Analysis

A total of 43 patients were recruited into the study including 16 patients belonging to the first stage and 27 belonging to the second stage. These patients received NGR-hTNF at dose of 0.8 µg/m$^2$ by a 60-minute iv infusion every 3 weeks (q3w). Sixty-three percent of patients were males; the median age was 64 years old (range 54 to 80 years); ECOG performance status was 0 (24 pts) 1 (10 pts) and 2 (9 pts) respectively. Most of the patients (79%) had epithelial MPM in comparison with nonepithelial histology (21%). Overall, 170 cycles (median 2, range 1-18 cycles) were completed. One patient (2%) had a partial response (the patient is currently progression-free after 14.3 months) and eighteen patients (42%) had a stable disease (SD) with a median duration of 4.4 months (range 2.2-13.7+). The maximum changes of target lesion in SD patients ranged from 17% shrinkage to 6% growth. The estimated PFS was 2.8 months (95% CI, 1.9-3.7 months). An elderly patient with a performance status of 2 and a patient completely refractory to prior therapy experienced prolonged progression-free times of 10.9 and 10.5 months, respectively. After a median follow-up time of nine months the median survival has not reached yet.

Patients Treated According to Protocol Amendment

Furthermore, at completion of second-stage of the study and as per protocol amendment, an additional 14 patients were enrolled in a subsequent cohort exploring NGR-hTNF given at same dose of 0.8 µg/m$^2$ on a weekly basis. Weekly dosing schedule did not change the pattern of NGR-hTNF toxicity. Moreover, there was no increase of either severity or frequency of adverse events. Furthermore, neither grade 3-4 drug-related toxicities nor toxicity-related deaths were reported. All patients were assessable for response and seven (50%) had SD for a median duration of 8.1 months. The median progression-free survival was 3.0 months. These further data on the weekly cohort confirmed the safe toxicity profile and efficacy of NGR-hTNF.

CONCLUSIONS

Taken together, the overall results obtained by NGR-hTNF on 57 patients (43 treated with a triweekly schedule and 14 with the weekly schedule), have confirmed its important role as second-line therapy in the treatment of advanced MPM. In this setting, only pemetrexed showed clinical benefit in terms of progression-free survival (3.6 months) when compared to best supportive care alone (1.5 months). However, considering that a pemetrexed-based combination regimen is the first-line treatment of choice, there are no currently available standard second-line therapy for MPM patients progressing after a first-line therapy (that is, the totality of patients). Particularly, NGR-hTNF doubled the progression-free survival observed with best supportive care alone that remains the reference approach for this patient population lacking a standard therapy. Moreover, these efficacy results obtained by NGR-hTNF as single agent are also comparable with best results obtained by either the combination of two chemotherapy agents (gemcitabine plus vinorelbine) and two targeted agents (bevacizumab plus erlotinib) or single agent (sunitinib), without the severe toxicities associated to these agents. Finally, after a median follow-up of 9 months, the median survival has not reached yet. Therefore, the median overall survival obtained with NGR-hTNF 5 therapy will be surely longer than the median survival registered with either active treatments or best supportive care alone in this setting, that is approximately of 8-9 months.

Main grade 1-2 toxicities per patient were infusion-related constitutional symptoms including chills (71%) and fatigue (36%). Only one patient had a grade 3 treatment-related toxicity and neither grade 4 treatment—related adverse event nor toxicity—related death were observed.

In conclusion, NGR-hTNF shows a favourable and manageable toxicity profile, with evidence of long lasting disease control in chemo-pre-treated MPM patients.

The invention claimed is:

1. A method for treating mesothelioma in a patient comprising administering to a patient suffering from mesothelioma a conjugate comprising a targeting peptide and a cytokine, wherein the targeting peptide is a peptide containing a NGR motif and wherein the cytokine is TNFα.

2. The method of claim 1 wherein the targeting peptide is selected from the group consisting of linear or cyclic CNGRCVSGCAGRC (SEQ ID No. 1), NGRAHA (SEQ ID No. 2), GNGRG (SEQ ID No. 3), CVLNGRMEC (SEQ ID No. 4), CNGRC (SEQ ID No. 5), CNGRCG (SEQ ID No. 6), LNGRE (SEQ ID No. 7), YNGRT (SEQ ID No. 8), LQCICTGNGRGEWKCE (SEQ ID No. 9), LQCISTGN-GRGEWKCE (SEQ ID No. 10), CICTGNGRGEWKC (SEQ ID No. 11), CISTGNGRGEWKC (SEQ ID No. 12), MRCTCVGNGRGEWTCY (SEQ ID No. 13), MRCTS-VGNGRGEWTCY (SEQ ID No. 14), CTCVGNGRGEWTC (SEQ ID No. 15) and CTSVGNGRGEWTC (SEQ ID No. 16).

3. The method of claim 1 wherein the cytokine is TNFα that is linked to a targeting peptide CNGRC (SEQ ID No. 5) through a spacer G (glycine).

4. The method of claim 1 wherein the conjugate is administered to the patient at a dose of 0.8 μg/m² by a 60 minute intravenous infusion every three weeks.

5. The method of claim 1 wherein the conjugate is administered to the patient at a dose of 0.8 μg/m² by a 60 minute intravenous infusion every week.

6. The method of claim 3, wherein the patient is a human.

7. A method for treating mesothelioma in a patient comprising administering to a patient suffering from mesothelioma a pharmaceutical composition comprising an effective amount of a conjugate comprising a targeting peptide and a cytokine, wherein the targeting peptide is a peptide containing a NGR motif and wherein the cytokine is TNFα together with pharmaceutically acceptable carriers and diluents.

8. The method of claim 7 wherein the conjugate comprises TNFα that is linked to a targeting peptide CNGRC (SEQ ID No. 5) through a spacer G (glycine).

9. The method of claim 7 wherein the effective amount of the conjugate is at a concentration in the range of 0.01 to 10 mg/ml.

10. The method of claim 7 wherein the pharmaceutical formulation consists of 0.150 mg/ml of a conjugate comprising TNFα linked to the targeting peptide CNGRC (SEQ ID No. 5) through the spacer G dissolved in a solution of 50mM Na2HPO4, 150 mM NaCl.

11. The method of claim 7 wherein the patient is a human.

* * * * *

SEQUENCE LISTING

```
<160> NUMBER OF SEQ ID NOS: 32

<210> SEQ ID NO 1
<211> LENGTH: 13
<212> TYPE: PRT
<213> ORGANISM: Artificial sequence
<220> FEATURE:
<223> OTHER INFORMATION: Description of Artificial Sequence: targeting
      peptide
```

```
<400> SEQUENCE: 1

Cys Asn Gly Arg Cys Val Ser Gly Cys Ala Gly Arg Cys
1               5                   10

<210> SEQ ID NO 2
<211> LENGTH: 6
<212> TYPE: PRT
<213> ORGANISM: Artificial sequence
<220> FEATURE:
<223> OTHER INFORMATION: Description of Artificial Sequence: targeting
      peptide

<400> SEQUENCE: 2

Asn Gly Arg Ala His Ala
1               5

<210> SEQ ID NO 3
<211> LENGTH: 5
<212> TYPE: PRT
<213> ORGANISM: Artificial sequence
<220> FEATURE:
<223> OTHER INFORMATION: Description of Artificial Sequence: targeting
      peptide

<400> SEQUENCE: 3

Gly Asn Gly Arg Gly
1               5

<210> SEQ ID NO 4
<211> LENGTH: 9
<212> TYPE: PRT
<213> ORGANISM: Artificial sequence
<220> FEATURE:
<223> OTHER INFORMATION: Description of Artificial Sequence: targeting
      peptide

<400> SEQUENCE: 4

Cys Val Leu Asn Gly Arg Met Glu Cys
1               5

<210> SEQ ID NO 5
<211> LENGTH: 5
<212> TYPE: PRT
<213> ORGANISM: Artificial sequence
<220> FEATURE:
<223> OTHER INFORMATION: Description of Artificial Sequence: targeting
      peptide

<400> SEQUENCE: 5

Cys Asn Gly Arg Cys
1               5

<210> SEQ ID NO 6
<211> LENGTH: 6
<212> TYPE: PRT
<213> ORGANISM: Artificial sequence
<220> FEATURE:
<223> OTHER INFORMATION: Description of Artificial Sequence: targeting
      peptide

<400> SEQUENCE: 6

Cys Asn Gly Arg Cys Gly
1               5

<210> SEQ ID NO 7
<211> LENGTH: 5
<212> TYPE: PRT
```

```
<213> ORGANISM: Artificial sequence
<220> FEATURE:
<223> OTHER INFORMATION: Description of Artificial Sequence: targeting
      peptide

<400> SEQUENCE: 7

Leu Asn Gly Arg Glu
1               5

<210> SEQ ID NO 8
<211> LENGTH: 5
<212> TYPE: PRT
<213> ORGANISM: Artificial sequence
<220> FEATURE:
<223> OTHER INFORMATION: Description of Artificial Sequence: targeting
      peptide

<400> SEQUENCE: 8

Tyr Asn Gly Arg Thr
1               5

<210> SEQ ID NO 9
<211> LENGTH: 16
<212> TYPE: PRT
<213> ORGANISM: Artificial sequence
<220> FEATURE:
<223> OTHER INFORMATION: Description of Artificial Sequence: targeting
      peptide

<400> SEQUENCE: 9

Leu Gln Cys Ile Cys Thr Gly Asn Gly Arg Gly Glu Trp Lys Cys Glu
1               5                   10                  15

<210> SEQ ID NO 10
<211> LENGTH: 16
<212> TYPE: PRT
<213> ORGANISM: Artificial sequence
<220> FEATURE:
<223> OTHER INFORMATION: Description of Artificial Sequence: targeting
      peptide

<400> SEQUENCE: 10

Leu Gln Cys Ile Ser Thr Gly Asn Gly Arg Gly Glu Trp Lys Cys Glu
1               5                   10                  15

<210> SEQ ID NO 11
<211> LENGTH: 13
<212> TYPE: PRT
<213> ORGANISM: Artificial sequence
<220> FEATURE:
<223> OTHER INFORMATION: Description of Artificial Sequence: targeting
      peptide

<400> SEQUENCE: 11

Cys Ile Cys Thr Gly Asn Gly Arg Gly Glu Trp Lys Cys
1               5                   10

<210> SEQ ID NO 12
<211> LENGTH: 13
<212> TYPE: PRT
<213> ORGANISM: Artificial sequence
<220> FEATURE:
<223> OTHER INFORMATION: Description of Artificial Sequence: targeting
      peptide

<400> SEQUENCE: 12

Cys Ile Ser Thr Gly Asn Gly Arg Gly Glu Trp Lys Cys
1               5                   10
```

```
<210> SEQ ID NO 13
<211> LENGTH: 16
<212> TYPE: PRT
<213> ORGANISM: Artificial sequence
<220> FEATURE:
<223> OTHER INFORMATION: Description of Artificial Sequence: targeting
      peptide

<400> SEQUENCE: 13

Met Arg Cys Thr Cys Val Gly Asn Gly Arg Gly Glu Trp Thr Cys Tyr
1               5                   10                  15

<210> SEQ ID NO 14
<211> LENGTH: 16
<212> TYPE: PRT
<213> ORGANISM: Artificial sequence
<220> FEATURE:
<223> OTHER INFORMATION: Description of Artificial Sequence: targeting
      peptide

<400> SEQUENCE: 14

Met Arg Cys Thr Ser Val Gly Asn Gly Arg Gly Glu Trp Thr Cys Tyr
1               5                   10                  15

<210> SEQ ID NO 15
<211> LENGTH: 13
<212> TYPE: PRT
<213> ORGANISM: Artificial sequence
<220> FEATURE:
<223> OTHER INFORMATION: Description of Artificial Sequence: targeting
      peptide

<400> SEQUENCE: 15

Cys Thr Cys Val Gly Asn Gly Arg Gly Glu Trp Thr Cys
1               5                   10

<210> SEQ ID NO 16
<211> LENGTH: 13
<212> TYPE: PRT
<213> ORGANISM: Artificial sequence
<220> FEATURE:
<223> OTHER INFORMATION: Description of Artificial Sequence: targeting
      peptide

<400> SEQUENCE: 16

Cys Thr Ser Val Gly Asn Gly Arg Gly Glu Trp Thr Cys
1               5                   10

<210> SEQ ID NO 17
<211> LENGTH: 13
<212> TYPE: PRT
<213> ORGANISM: Artificial sequence
<220> FEATURE:
<223> OTHER INFORMATION: Description of Artificial Sequence: targeting
      peptide
<220> FEATURE:
<221> NAME/KEY: MOD_RES
<222> LOCATION: (2)..(2)
<223> OTHER INFORMATION: Xaa is isoaspartic acid

<400> SEQUENCE: 17

Cys Xaa Gly Arg Cys Val Ser Gly Cys Ala Gly Arg Cys
1               5                   10

<210> SEQ ID NO 18
<211> LENGTH: 6
<212> TYPE: PRT
```

```
<213> ORGANISM: Artificial sequence
<220> FEATURE:
<223> OTHER INFORMATION: Description of Artificial Sequence: targeting
      peptide
<220> FEATURE:
<221> NAME/KEY: MOD_RES
<222> LOCATION: (1)..(1)
<223> OTHER INFORMATION: Xaa is iso-aspartic acid (isoD)

<400> SEQUENCE: 18

Xaa Gly Arg Ala His Ala
1               5

<210> SEQ ID NO 19
<211> LENGTH: 5
<212> TYPE: PRT
<213> ORGANISM: Artificial sequence
<220> FEATURE:
<223> OTHER INFORMATION: Description of Artificial Sequence: targeting
      peptide
<220> FEATURE:
<221> NAME/KEY: MOD_RES
<222> LOCATION: (2)..(2)
<223> OTHER INFORMATION: Xaa is iso-aspartic acid (isoD)

<400> SEQUENCE: 19

Gly Xaa Gly Arg Gly
1               5

<210> SEQ ID NO 20
<211> LENGTH: 9
<212> TYPE: PRT
<213> ORGANISM: Artificial sequence
<220> FEATURE:
<223> OTHER INFORMATION: Description of Artificial Sequence: targeting
      peptide
<220> FEATURE:
<221> NAME/KEY: MOD_RES
<222> LOCATION: (4)..(4)
<223> OTHER INFORMATION: Xaa is iso-aspartic acid (isoD)

<400> SEQUENCE: 20

Cys Val Leu Xaa Gly Arg Met Glu Cys
1               5

<210> SEQ ID NO 21
<211> LENGTH: 5
<212> TYPE: PRT
<213> ORGANISM: Artificial sequence
<220> FEATURE:
<223> OTHER INFORMATION: Description of Artificial Sequence: targeting
      peptide
<220> FEATURE:
<221> NAME/KEY: MOD_RES
<222> LOCATION: (2)..(2)
<223> OTHER INFORMATION: Xaa is iso-aspartic acid (isoD)

<400> SEQUENCE: 21

Cys Xaa Gly Arg Cys
1               5

<210> SEQ ID NO 22
<211> LENGTH: 6
<212> TYPE: PRT
<213> ORGANISM: Artificial sequence
<220> FEATURE:
<223> OTHER INFORMATION: Description of Artificial Sequence: targeting
      peptide
<220> FEATURE:
<221> NAME/KEY: MOD_RES
<222> LOCATION: (2)..(2)
```

```
<223> OTHER INFORMATION: Xaa is iso-aspartic acid (isoD)

<400> SEQUENCE: 22

Cys Xaa Gly Arg Cys Gly
1               5

<210> SEQ ID NO 23
<211> LENGTH: 5
<212> TYPE: PRT
<213> ORGANISM: Artificial sequence
<220> FEATURE:
<223> OTHER INFORMATION: Description of Artificial Sequence: targeting
      peptide
<220> FEATURE:
<221> NAME/KEY: MOD_RES
<222> LOCATION: (2)..(2)
<223> OTHER INFORMATION: Xaa is iso-aspartic acid (isoD)

<400> SEQUENCE: 23

Leu Xaa Gly Arg Glu
1               5

<210> SEQ ID NO 24
<211> LENGTH: 5
<212> TYPE: PRT
<213> ORGANISM: Artificial sequence
<220> FEATURE:
<223> OTHER INFORMATION: Description of Artificial Sequence: targeting
      peptide
<220> FEATURE:
<221> NAME/KEY: MOD_RES
<222> LOCATION: (2)..(2)
<223> OTHER INFORMATION: Xaa is iso-aspartic acid (isoD)

<400> SEQUENCE: 24

Tyr Xaa Gly Arg Thr
1               5

<210> SEQ ID NO 25
<211> LENGTH: 16
<212> TYPE: PRT
<213> ORGANISM: Artificial sequence
<220> FEATURE:
<223> OTHER INFORMATION: Description of Artificial Sequence: targeting
      peptide
<220> FEATURE:
<221> NAME/KEY: MOD_RES
<222> LOCATION: (8)..(8)
<223> OTHER INFORMATION: Xaa is iso-aspartic acid (isoD)

<400> SEQUENCE: 25

Leu Gln Cys Ile Cys Thr Gly Xaa Gly Arg Gly Glu Trp Lys Cys Glu
1               5                   10                  15

<210> SEQ ID NO 26
<211> LENGTH: 16
<212> TYPE: PRT
<213> ORGANISM: Artificial sequence
<220> FEATURE:
<223> OTHER INFORMATION: Description of Artificial Sequence: targeting
      peptide
<220> FEATURE:
<221> NAME/KEY: MOD_RES
<222> LOCATION: (8)..(8)
<223> OTHER INFORMATION: Xaa is iso-aspartic acid (isoD)

<400> SEQUENCE: 26

Leu Gln Cys Ile Ser Thr Gly Xaa Gly Arg Gly Glu Trp Lys Cys Glu
1               5                   10                  15
```

```
<210> SEQ ID NO 27
<211> LENGTH: 13
<212> TYPE: PRT
<213> ORGANISM: Artificial sequence
<220> FEATURE:
<223> OTHER INFORMATION: Description of Artificial Sequence: targeting
      peptide
<220> FEATURE:
<221> NAME/KEY: MOD_RES
<222> LOCATION: (6)..(6)
<223> OTHER INFORMATION: Xaa is iso-aspartic acid (isoD)

<400> SEQUENCE: 27

Cys Ile Cys Thr Gly Xaa Gly Arg Gly Glu Trp Lys Cys
1               5                   10

<210> SEQ ID NO 28
<211> LENGTH: 13
<212> TYPE: PRT
<213> ORGANISM: Artificial sequence
<220> FEATURE:
<223> OTHER INFORMATION: Description of Artificial Sequence: targeting
      peptide
<220> FEATURE:
<221> NAME/KEY: MOD_RES
<222> LOCATION: (6)..(6)
<223> OTHER INFORMATION: Xaa is iso-aspartic acid (isoD)

<400> SEQUENCE: 28

Cys Ile Ser Thr Gly Xaa Gly Arg Gly Glu Trp Lys Cys
1               5                   10

<210> SEQ ID NO 29
<211> LENGTH: 16
<212> TYPE: PRT
<213> ORGANISM: Artificial sequence
<220> FEATURE:
<223> OTHER INFORMATION: Description of Artificial Sequence: targeting
      peptide
<220> FEATURE:
<221> NAME/KEY: MOD_RES
<222> LOCATION: (8)..(8)
<223> OTHER INFORMATION: Xaa is iso-aspartic acid (isoD)

<400> SEQUENCE: 29

Met Arg Cys Thr Cys Val Gly Xaa Gly Arg Gly Glu Trp Thr Cys Tyr
1               5                   10                  15

<210> SEQ ID NO 30
<211> LENGTH: 16
<212> TYPE: PRT
<213> ORGANISM: Artificial sequence
<220> FEATURE:
<223> OTHER INFORMATION: Description of Artificial Sequence: targeting
      peptide
<220> FEATURE:
<221> NAME/KEY: MOD_RES
<222> LOCATION: (8)..(8)
<223> OTHER INFORMATION: Xaa is iso-aspartic acid (isoD)

<400> SEQUENCE: 30

Met Arg Cys Thr Ser Val Gly Xaa Gly Arg Gly Glu Trp Thr Cys Tyr
1               5                   10                  15

<210> SEQ ID NO 31
<211> LENGTH: 13
<212> TYPE: PRT
<213> ORGANISM: Artificial sequence
<220> FEATURE:
<223> OTHER INFORMATION: Description of Artificial Sequence: targeting
```

```
    peptide
<220> FEATURE:
<221> NAME/KEY: MOD_RES
<222> LOCATION: (6)..(6)
<223> OTHER INFORMATION: Xaa is iso-aspartic acid (isoD)

<400> SEQUENCE: 31

Cys Thr Cys Val Gly Xaa Gly Arg Gly Glu Trp Thr Cys
1               5                   10

<210> SEQ ID NO 32
<211> LENGTH: 13
<212> TYPE: PRT
<213> ORGANISM: Artificial sequence
<220> FEATURE:
<223> OTHER INFORMATION: Description of Artificial Sequence: targeting
      peptide
<220> FEATURE:
<221> NAME/KEY: MOD_RES
<222> LOCATION: (6)..(6)
<223> OTHER INFORMATION: Xaa is iso-aspartic acid (isoD)

<400> SEQUENCE: 32

Cys Thr Ser Val Gly Xaa Gly Arg Gly Glu Trp Thr Cys
1               5                   10
```